(12) United States Patent
Chinzei et al.

(10) Patent No.: US 12,297,420 B2
(45) Date of Patent: May 13, 2025

(54) AGENT FOR REGULATING CONCENTRATION OF GAS FOR ANAEROBIC BACTERIUM CULTURE AND METHOD FOR CULTURING ANAEROBIC BACTERIUM USING SAME

(71) Applicant: MITSUBISHI GAS CHEMICAL COMPANY, INC., Tokyo (JP)

(72) Inventors: Tatsuya Chinzei, Tokyo (JP); Masao Someya, Tokyo (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 748 days.

(21) Appl. No.: 17/619,799

(22) PCT Filed: Jun. 8, 2020

(86) PCT No.: PCT/JP2020/022460
§ 371 (c)(1),
(2) Date: Dec. 16, 2021

(87) PCT Pub. No.: WO2020/261951
PCT Pub. Date: Dec. 30, 2020

(65) Prior Publication Data
US 2022/0325224 A1    Oct. 13, 2022

(30) Foreign Application Priority Data
Jun. 24, 2019 (JP) ................. 2019-116715

(51) Int. Cl.
*C12N 1/20* (2006.01)
*C12M 1/34* (2006.01)

(52) U.S. Cl.
CPC ............ *C12M 41/34* (2013.01); *C12M 41/30* (2013.01); *C12M 41/46* (2013.01); *C12N 1/20* (2013.01)

(58) Field of Classification Search
None
See application file for complete search history.

(56) References Cited

U.S. PATENT DOCUMENTS

| | | | |
|---|---|---|---|
| 6,114,162 | A | 9/2000 | Kashiba |
| 2012/0282690 | A1 | 11/2012 | Oura et al. |
| 2018/0298322 | A1 | 10/2018 | Bjork et al. |
| 2019/0282996 | A1 | 9/2019 | Thatte |

FOREIGN PATENT DOCUMENTS

| | | |
|---|---|---|
| CN | 102639698 A | 8/2012 |
| EP | 0 111 583 A1 | 6/1984 |
| JP | 1-202281 A | 8/1989 |
| JP | 10-327845 A | 12/1998 |
| JP | 3818324 B2 | 9/2006 |
| JP | 5682831 B2 | 3/2015 |
| JP | 2018-514213 A | 6/2018 |
| KR | 10-2006-0118908 A | 11/2006 |
| WO | 2018/101944 A1 | 6/2018 |

OTHER PUBLICATIONS

International Search Report issued in International Patent Application No. PCT/JP2020/022460, dated Aug. 11, 2020, along with an English translation thereof.

Written Opinion of the International Searching Authority issued in International Patent Application No. PCT/JP2020/022460, dated Aug. 11, 2020, along with an English translation thereof.

*Primary Examiner* — Neil N Turk
(74) *Attorney, Agent, or Firm* — GREENBLUM & BERNSTEIN P.L.C.

(57) ABSTRACT

A gas concentration regulator for use in culture of anaerobic bacteria, including: (a) dehydroascorbic acid; (c) a transition metal catalyst; (d) activated carbon; (e) at least one selected from the group consisting of an alkali metal carbonate, an alkali metal hydroxide, and an alkaline earth metal hydroxide; and (f) water.

4 Claims, No Drawings

AGENT FOR REGULATING CONCENTRATION OF GAS FOR ANAEROBIC BACTERIUM CULTURE AND METHOD FOR CULTURING ANAEROBIC BACTERIUM USING SAME

TECHNICAL FIELD

The present invention relates to a gas concentration regulator for use in culture of anaerobic bacteria and a method for culturing anaerobic bacteria using the same.

BACKGROUND ART

In culture of biological samples such as tissues or cells performed in research fields or industrial fields of biology, reproduction, or biotechnology, a gas environment that differs from the atmosphere is required. For example, it is necessary to set an atmospheric carbon dioxide concentration to about 5% as a condition to keep the pH of a bicarbonate buffer-based culture solution at pH 7.4, which is the same as pH of blood in the normal state. Further, in many research fields, culture of cells in a low-concentration oxygen atmosphere similar to that in vivo has been performed.

As a means for producing a gas environment with a high-concentration carbon dioxide atmosphere and a low-concentration oxygen atmosphere, a carbon dioxide gas incubator is known; however, there are issues such as the financial burden on equipment and management of high-pressure gases. Accordingly, in recent years, there has been widely used a method in which a gas concentration regulator utilizing an oxidation reaction of an ascorbic acid component is used (see Patent Documents 1 and 2).

CITATION LIST

Patent Documents

Patent Document 1: JP 3818324 B
Patent Document 2: JP 5682831 B

SUMMARY OF INVENTION

Technical Problem

In culture of anaerobic bacteria, it is required to produce a gas environment with a high-concentration carbon dioxide atmosphere. Thus, it is desirable to more efficiently increase an amount of carbon dioxide generated in an oxidation reaction of an ascorbic acid component.

The problem to be solved by the present invention is to provide a gas concentration regulator for use in culture of anaerobic bacteria that generates a large amount of carbon dioxide.

Solution to Problem

As a result of diligent research, the present inventor has found that an amount of carbon dioxide generated increases when dehydroascorbic acid is blended as compared to a case where ascorbic acid is blended. The present invention has been completed based on such finding.

That is, the present invention relates to the following.

<1> A gas concentration regulator for use in culture of anaerobic bacteria, including: (a) dehydroascorbic acid; (c) a transition metal catalyst; (d) activated carbon; (e) at least one selected from the group consisting of an alkali metal carbonate, an alkali metal hydroxide, and an alkaline earth metal hydroxide; and (f) water.

<2> The gas concentration regulator for use in culture of anaerobic bacteria according to <1> above, further including (b) an ascorbic acid component.

<3> The gas concentration regulator for use in culture of anaerobic bacteria according to <2> above, wherein a molar ratio [(b)/(a)] of (b) the ascorbic acid component to (a) the dehydroascorbic acid is 1.5 or less.

<4> A method for culturing anaerobic bacteria, including culturing anaerobic bacteria in the presence of the gas concentration regulator according to any one of <1> to <3> above.

<5> A gas concentration regulator package, in which the gas concentration regulator according to any one of <1> to <3> above is bagged in an individual bag using an air-permeable packaging material.

Advantageous Effects of Invention

The gas concentration regulator for use in culture of anaerobic bacteria according to the present invention generates a large amount of carbon dioxide, so that it is possible to efficiently produce a gas environment with a high-concentration carbon dioxide atmosphere and a low-concentration oxygen atmosphere.

DESCRIPTION OF EMBODIMENTS

An embodiment according to the present invention will be described below. The content of the present invention is not limited to the embodiment described below.

Note that in the present specification, a phrase of "A to B" indicating a numerical range means "more than or equal to A and less than or equal to B" (in the case of A<B), or "less than or equal to A and more than or equal to B" (in the case of A>B). Furthermore, in the present invention, a combination of preferable aspects is a more preferable aspect.

[Gas Concentration Regulator]

A gas concentration regulator for use in culture of anaerobic bacteria according to the present invention includes: (a) dehydroascorbic acid; (c) a transition metal catalyst; (d) activated carbon; (e) at least one selected from the group consisting of an alkali metal carbonate, an alkali metal hydroxide, and an alkaline earth metal hydroxide; and (f) water. The gas concentration regulator may further include (b) an ascorbic acid component.

Further, the gas concentration regulator according to the present invention is preferably used as a package in which a composition including (a) dehydroascorbic acid, (c) a transition metal catalyst, (d) activated carbon, (e) at least one selected from the group consisting of an alkali metal carbonate, an alkali metal hydroxide, and an alkaline earth metal hydroxide, and (f) water is bagged using an air-permeable packaging material. The composition may further include (b) an ascorbic acid component.

The gas concentration regulator according to the present invention includes the components (a) to (f) in an amount of preferably 50 mass % or more, more preferably 60 mass % or more, and even more preferably 70 mass % or more in total.

(a) Dehydroascorbic Acid

The gas concentration regulator according to the present invention includes dehydroascorbic acid having both an oxygen absorption capacity and a carbon dioxide gas generation capacity as a main agent of an oxygen absorption reaction.

The dehydroascorbic acid is a compound obtained by oxidizing ascorbic acid, which produces diketogulonic acid by hydrolysis. And then, a catalyst and a reaction environment are appropriately adjusted, so that a decarboxylation reaction and an oxidation reaction are repeated to generate carbon dioxide and absorb oxygen. The dehydroascorbic acid can also be produced by oxidizing an ascorbic acid component.

In the gas concentration regulator according to the present invention, activated carbon is preferable impregnated with the dehydroascorbic acid and water from the viewpoint of oxygen absorption performance Specifically, the activated carbon, which is a porous carrier, is preferably impregnated with an aqueous solution of the dehydroascorbic acid in which the dehydroascorbic acid is dissolved in water.

In the gas concentration regulator, the oxidation reaction of the dehydroascorbic acid is utilized to absorb oxygen in the atmosphere, thereby adjusting the concentration thereof, and carbon dioxide generated by the oxidation reaction is utilized to adjust the carbon dioxide concentration in the atmosphere. Note that in the oxidation reaction, carbon dioxide is theoretically generated in a molar amount equivalent to or more than that of oxygen molecules consumed. In accordance with the above principles, when the oxygen concentration is reduced, the carbon dioxide concentration increases.

(b) Ascorbic Acid Component

The gas concentration regulator according to the present invention may include an ascorbic acid component. The ascorbic acid is readily available at a low cost as compared to the dehydroascorbic acid, and has both oxygen absorption capacity and carbon dioxide generation capacity as a main agent for the oxygen absorption reaction.

The ascorbic acid component means L-ascorbic acid and stereoisomers thereof, as well as salts and hydrates thereof. Examples of L-ascorbic acid salts include sodium L-ascorbate, potassium L-ascorbate, calcium L-ascorbate, and the like. Examples of stereoisomers of L-ascorbic acid include erythorbic acid (D-isoascorbic acid) and the like. Examples of erythorbic acid salts include sodium erythorbate, potassium erythorbate, calcium erythorbate, and the like. One ascorbic acid component may be used alone, or two or more may be used in combination.

In the gas concentration regulator according to the present invention, activated carbon is preferably impregnated with the ascorbic acid component and water from the viewpoint of oxygen absorption performance Specifically, the activated carbon, which is a porous carrier, is preferable impregnated with an aqueous solution of the ascorbic acid component in which the ascorbic acid component is dissolved in water. At this time, when the concentration of the ascorbic acid component in the aqueous solution is higher, the usage amount of the porous carrier can be reduced, and thus it is preferable to make the concentration of the ascorbic acid component at a concentration as close as possible to the saturation solubility. Due to this, it is preferable to select, as the ascorbic acid component, a compound having a high solubility in water. Ascorbic acid or sodium ascorbate is preferable as the ascorbic acid component from the viewpoint of solubility in water and ease of availability. When ascorbic acid or sodium ascorbate is used, the concentration in the aqueous solution is suitably set to from 40 to 55 mass %.

When the gas concentration regulator according to the present invention includes (b) the ascorbic acid component, the molar ratio [(b)/(a)] of (b) the ascorbic acid component to (a) the dehydroascorbic acid is preferably 1.5 or less, more preferably 1.2 or less, even more preferably 1.0 or less, even more preferably 0.7 or less, even more preferably 0.5 or less, and even more preferably 0.1 or less. In culturing anaerobic bacteria, the gas concentration regulator is used in a gas-barrier sealed container and only needs to have the composition described above when it is put into the gas-barrier sealed container.

(c) Transition Metal Catalyst

The gas concentration regulator according to the present invention includes a transition metal catalyst that promotes progression of the oxidation reaction of the dehydroascorbic acid and the ascorbic acid component.

The transition metal catalyst is a catalyst having a metal compound such as a salt or an oxide of transition metal. Examples of suitable transition metal include iron, manganese, zinc, copper, and cobalt. Examples of the salt of transition metal include halides and mineral acid salts of transition metal, for example, chlorides and sulfates of transition metal. Representative examples thereof include anhydrates or hydrates of ferrous chloride, ferric chloride, ferrous sulfate, ferric sulfate, manganese chloride, zinc sulfate, copper sulfate, copper chloride, and cobalt sulfate, and among these, ferrous sulphate heptahydrate with good solubility in water and good compounding property is preferable.

From the viewpoint of promoting progression of the oxidation reaction of the dehydroascorbic acid and the ascorbic acid component, the content of the transition metal catalyst in the gas concentration regulator is preferably from 1 to 30 parts by mass, more preferably from 5 to 25 parts by mass, and even more preferably from 10 to 20 parts by mass per a total of 100 parts by mass of the dehydroascorbic acid and the ascorbic acid component.

(d) Activated Carbon

The gas concentration regulator according to the present invention includes activated carbon. The activated carbon functions as a carrier of being impregnated with the aqueous solution of the dehydroascorbic acid and the aqueous solution of the ascorbic acid component, and has a function of promoting progression of the oxidation reaction because the activated carbon has a large contact area with air due to its large specific surface area.

As the activated carbon, there can be used what is produced using sawdust, coal, a palm shell, or the like as a raw material by various production methods such as water vapor activation or agent activation using zinc chloride or the like. Furthermore, the activated carbon is used to support the aqueous solution of the dehydroascorbic acid, the aqueous solution of the ascorbic acid component, or the like and filled in an individual bag in a granular form, and thus granular activated carbon is preferable. The particle diameter of the granular activated carbon is preferably from 0.1 to 2 mm, and more preferably from 0.5 to 1 mm, from the viewpoint of oxygen absorption performance and a filling property (flowability) into a package.

The content of the activated carbon in the gas concentration regulator is preferably 50 to 400 parts by mass and more preferably from 75 to 300 parts by mass per a total of 100 parts by mass of the dehydroascorbic acid and the ascorbic acid component, from the viewpoint of the oxygen absorption performance and the filling property into the package.

(e) Alkali Metal Carbonate, Alkali Metal Hydroxide, and Alkaline Earth Metal Hydroxide The gas concentration regulator according to the present invention includes at least one selected from the group consisting of an alkali metal carbonate, an alkali metal hydroxide, and an alkaline earth metal hydroxide. At least one selected from the group consisting of an alkali metal carbonate, an alkali metal hydroxide, and an alkaline earth metal hydroxide is used to cause the oxidation reaction of the dehydroascorbic acid and the ascorbic acid component to rapidly proceed and to control a reaction field to an alkaline region.

As the alkali metal carbonate, a water-soluble alkali metal carbonate such as sodium carbonate, sodium hydrogen carbonate, or sodium carbonate hydrate is suitably used, and among them, sodium carbonate is particularly preferable.

Examples of the alkali metal hydroxide include potassium hydroxide and sodium hydroxide, and of these, sodium hydroxide is preferable.

Examples of the alkaline earth metal hydroxide include calcium hydroxide and magnesium hydroxide.

Among the alkali metal carbonate, the alkali metal hydroxide, and the alkaline earth metal hydroxide, the gas concentration regulator according to the present invention preferably includes an alkali metal carbonate and/or an alkali metal hydroxide from the viewpoint of solubility in water when becoming a salt with ascorbic acid.

The content of the alkali metal hydroxide in the gas concentration regulator is preferably an equimolar amount relative to the total molar amount of the dehydroascorbic acid and the ascorbic acid component from the viewpoint of neutralizing a hydrolytic product.

The content of the alkali metal carbonate in the gas concentration regulator is preferably from 10 to 200 parts by mass, more preferably from 50 to 200 parts by mass, and even more preferably from 100 to 150 parts by mass, per a total of 100 parts by mass of the dehydroascorbic acid and the ascorbic acid component, from the viewpoint of adjusting the carbon dioxide concentration.

(f) Water

The gas concentration regulator according to the present invention includes water necessary for the oxidation reaction of the dehydroascorbic acid and the ascorbic acid component to proceed.

It is preferable to adopt an aspect in which the activated carbon is impregnated with water from the viewpoint that the gas concentration regulator can be obtained as a solid with fluidity. In the gas concentration regulator according to the present invention, the activated carbon is preferably impregnated with water as well as the dehydroascorbic acid and the ascorbic acid component from the viewpoint of oxygen absorption performance Specifically, the activated carbon, which is a porous carrier, is preferably impregnated with an aqueous solution of the dehydroascorbic acid in which the dehydroascorbic acid is dissolved in water and an aqueous solution of the ascorbic acid component in which the ascorbic acid component is dissolved in water. Furthermore, soluble components other than the dehydroascorbic acid and the ascorbic acid component may be dissolved in water, or insoluble components may be dispersed in water.

The content of water in the gas concentration regulator is preferably from 30 to 500 parts by mass, more preferably from 50 to 300 parts by mass, and even more preferably from 80 to 200 parts by mass, per a total of 100 parts by mass of the dehydroascorbic acid and the ascorbic acid component, from the viewpoint of causing the oxidation reaction of the dehydroascorbic acid and the ascorbic acid component to proceed.

(g) Additional Component

The gas concentration regulator according to the present invention may include components other than the above-mentioned components (a) to (f) as needed within a range that does not inhibit the effects of the present invention.

(g1) Thermoplastic Resin

The gas concentration regulator according to the present invention may include a thermoplastic resin to suppress excessive heat generation associated with the progression of an oxygen absorption reaction (oxidation reaction of the dehydroascorbic acid and the ascorbic acid component). The type of the thermoplastic resin is not particularly limited, but for example, polyethylene, polypropylene, ethylene-vinyl acetate copolymer, elastomer, or a mixture thereof can be used, and in particular, low molecular weight polyethylene, polypropylene, or a mixture thereof having a molecular weight of 10000 or less is suitably used from the viewpoint of ease of adjusting a softening point and a low odor impact.

From the viewpoint of miscibility with other components, the thermoplastic resin is preferably a granular body with a particle diameter from 1 to 500 μm, and more preferably a granular body with a particle diameter from 10 to 300 μm. In addition, from the viewpoint of more effectively suppressing heat generation, the softening point of the thermoplastic resin is preferably 90 to 125° C.

The content of the thermoplastic resin in the gas concentration regulator is preferably from 100 to 1000 parts by mass and more preferably from 300 to 500 parts by mass per a total of 100 parts by mass of the dehydroascorbic acid and the ascorbic acid component, from the viewpoint of causing the oxidation reaction of the dehydroascorbic acid and the ascorbic acid component to proceed.

(g2) Aldehyde Removal Agent

The gas concentration regulator according to the present invention may include an aldehyde removal agent to remove aldehyde that is predominately generated as a by-product with the progression of the oxidation reaction of the dehydroascorbic acid and the ascorbic acid component. As a compound having an aldehyde removal capability, various compounds such as amines are known, but ethylene urea, urea, arginine, lysine hydrochloride, or polyallylamine, each of which has a sufficient aldehyde removal capability, does not generate an irritating odor, and exhibits a high effect in a small amount, is preferably compounded, and ethylene urea exhibiting a high effect in a smaller amount is more preferable.

The aldehyde referred to herein means a compound having one or more formyl groups in its molecule, that is, aldehydes. In the present invention, the aldehyde typically means aldehyde that is generated as a by-product in the course of oxygen absorption or culture of bacteria, and includes any aldehyde as long as it is classified in the chemical field into aldehydes and it adversely affects the culture of bacteria. Specific examples thereof include formaldehyde and acetaldehyde.

The content of the aldehyde removal agent in the gas concentration regulator is preferably from 0.5 to 25 parts by mass, more preferably from 1 to 10 parts by mass, and even more preferably from 1 to 5 parts by mass per a total of 100 parts by mass of the dehydroascorbic acid and the ascorbic acid component, from the viewpoint of efficiently and economically removing aldehyde.

(g3) Coating Material

The gas concentration regulator of the present invention may have a coating material on the outside of a granule of the composition including the components (a) to (f) described above. Examples of the coating material include porous particles of activated carbon, zeolite, silicates, or the like, from the viewpoint of adsorbing a trace amount of odor components generated by the oxygen absorption reaction. Furthermore, from the viewpoint of improving the fluidity of the gas concentration regulator and making it easy to fill the packaging material with the gas concentration regulator to be packaged, examples of the coating material include talc, magnesium stearate, calcium stearate, and the like. One type of these auxiliary agents can be used alone, or two or more types thereof can be used in combination as necessary. Furthermore, as these auxiliary agents, commercially available products can also be easily obtained.

(Method for Producing Gas Concentration Regulator)

A method for producing a gas concentration regulator according to the present invention is not particularly limited, but examples thereof include a method in which an aqueous solution of dehydroascorbic acid is prepared by dissolving the dehydroascorbic acid, a transition metal catalyst, an alkali metal hydroxide, and the like, and the obtained solution is mixed with activated carbon and an alkali metal carbonate, so that the activated carbon is impregnated with the solution. Furthermore, there is also a method in which an aqueous solution of an ascorbic acid component is prepared by dissolving the ascorbic acid component, a transition metal catalyst, an alkali metal hydroxide, and the like, an aqueous solution of dehydroascorbic acid is prepared by dissolving the dehydroascorbic acid, a transition metal catalyst, an alkali metal hydroxide, and the like, and these solutions are mixed with activated carbon and an alkali metal carbonate, so that the activated carbon is impregnated with the solutions.

[Gas Concentration Regulator Package]

The gas concentration regulator can be made into a gas concentration regulator package by packaging the composition containing the components described above by a packaging material using an air-permeable packaging material in whole or in part.

(Packaging Material)

Examples of the packaging material include a packaging material having a bag shape formed by bonding two sheets of an air-permeable packaging material to each other, a packaging material having a bag shape formed by bonding one sheet of an air-permeable packaging material and one sheet of a non-air-permeable packaging material to each other, and a packaging material having a bag shape formed by folding one sheet of an air-permeable packaging material and sealing edges other than the folded portion.

Here, when the air-permeable packaging material and the non-air-permeable packaging material each have a quadrilateral shape, examples of the packaging material include a packaging material having a bag shape formed by overlapping two sheets of an air-permeable packaging material and heat-sealing their four sides, a packaging material having a bag shape formed by overlapping one sheet of an air-permeable packaging material and one sheet of a non-air-permeable packaging material and heat-sealing their four sides, and a packaging material having a bag shape formed by folding one sheet of an air-permeable packaging material and heat-sealing its three sides other than the folded portion. Furthermore, the packaging material may be a packaging material having a bag shape formed by forming an air-permeable packaging material into a tubular shape and heat-sealing both ends and the trunk portion of the resulting tubular body.

(Air-Permeable Packaging Material)

As the air-permeable packaging material, a packaging material through which oxygen and carbon dioxide pass is selected. Of these, a packaging material having an air permeability resistance of 600 seconds or less, more preferably 90 seconds or less by a Gurley tester method is suitably used. Here, the air permeability resistance refers to a value measured by a method in accordance with JIS P 8117 (1998). More specifically, it refers to a time period required for 100 mL of air to pass through an air-permeable packaging material using a Gurley densometer available from Toyo Seiki Seisaku-sho, Ltd.

As the air-permeable packaging material, in addition to paper or nonwoven fabric, which is obtained by imparting air permeability to a plastic film is used. Examples of such a plastic film include a laminate film obtained by laminating and bonding a film of polyethylene terephthalate, polyamide, polypropylene, polycarbonate, or the like, and a film of polyethylene, an ionomer, polybutadiene, ethylene/acrylic acid copolymer, ethylene/methacrylic acid copolymer, ethylene/vinyl acetate copolymer, or the like as a sealing layer. These laminates can also be used as the air-permeable packaging material.

As the method of imparting air permeability, various methods can be employed, in addition to punching with a cold needle or a heat needle. When air permeability is imparted by punching, the air permeability can be freely adjusted by a diameter, the number, a material, and the like of holes to be punched.

The thickness of the laminated film is preferably from 50 to 300 μm, and particularly preferably from 60 to 250 μm. In this case, as compared to a case where the thickness deviates from the aforementioned range, the packaging material can be a packaging material that retains strength and has an excellent heat sealing property and packaging suitability.

In order to maintain the function for a long period of time, the gas concentration regulator package described above is preferably stored in a gas-barrier container or bag before use, and taken from the gas-barrier container or bag for use. In addition, when the gas concentration regulator package is used for utilization in culture of bacteria, it is preferable to perform sterilization using gamma radiation or the like on the package in advance.

[Method for Culturing Anaerobic Bacteria]

A method for culturing anaerobic bacteria according to the present invention is a method for culturing anaerobic bacteria in the presence of the gas concentration regulator. Specifically, the gas concentration regulator (preferably the gas concentration regulator package) is placed in a gas-barrier sealed container along with a culture vessel containing anaerobic bacteria and a medium, and then sealed, and the sealed container is allowed to stand at a suitable temperature for culture of bacteria.

The culture medium used in the culture method according to the present invention is not particularly limited, and the medium that is commonly used can be applied as is, so that the medium suitable for the bacteria to be cultured can be freely selected. The concentration of the aldehyde dissolved in the medium is preferably 2 mg/L or less, more preferably 1.5 mg/L or less, and even more preferably 1.0 mg/L or less, which is suitable as the bacteria culturing condition.

In addition, the culturing temperature is preferably 20 to 45° C., and particularly preferably 25 to 40° C.

The culture vessel is not particularly limited as long as the air permeability to the outside of the vessel is ensured, and any vessel having a volume, shape, material, or the like suitable for culturing can be used. A culture vessel having a lid portion is preferably used, but at this time as well, the air permeability to the outside of the vessel needs to be ensured.

The method for culturing bacteria according to the present invention is applied to culturing anaerobic bacteria. In the culture method according to the present invention, the atmosphere in the gas-barrier sealed container prior to culturing is not particularly limited, and the atmosphere may be air but is preferably a nitrogen atmosphere from the viewpoint of culturing anaerobic bacteria.

The gas-barrier sealed container used in the method for culturing bacteria prevents gas from flowing into/out of the container, and maintains the oxygen and carbon dioxide concentrations formed by the fed gas concentration regulator for a long period of time. A container made of glass, metal, plastic such as polycarbonate, or the like is often used, but it is also possible to use a gas-barrier film and a laminate thereof.

At this time, for the purpose of measuring an amount of aldehyde generated in the gas-barrier sealed container, adjusting a temperature in the container, or the like, an open container containing distilled water may be placed in the sealed container. As the open container, in addition to the culture vessel, a beaker, a flask, and the like can be exemplified, and a container of the same type as the culture vessel containing the bacteria and the medium is preferable.

From the viewpoint of culturing anaerobic bacteria, the oxygen concentration within the sealed container preferably turns 0.1 volume % or less within 24 hours. In addition, the carbon dioxide concentration in the sealed container is preferably 11.5 volume % or more, more preferably 12 volume % or more, even more preferably 13 volume % or more, and even more preferably 15 volume % or more.

In culture of bacteria, it is important to make a desired oxygen concentration and carbon dioxide concentration in a short time. From the viewpoint of culturing anaerobic bacteria, the oxygen concentration in the reaction initial stage (3 hours after reaction initiation) of the oxidation reaction of the dehydroascorbic acid and the ascorbic acid component is preferably 0.50 volume % or less, more preferably 0.30 volume % or less, and even more preferably 0.15 volume % or less. The carbon dioxide concentration in the reaction initial stage (3 hours after reaction initiation) of the oxidation reaction of the dehydroascorbic acid and the ascorbic acid component is preferably 11.5 volume % or more, more preferably 12 volume % or more, even more preferably 13 volume % or more, and even more preferably 15 volume % or more.

According to the culture method of the present invention, microscopic observation and transport of bacteria under a suitable gas atmosphere is enabled without using a gas cylinder and a gas controller.

EXAMPLES

Hereinafter, the present embodiment will be described in detail using Examples and Comparative Examples, but the present embodiment can be modified as appropriate as long as the present embodiment achieves the effects of the present invention. Note that "parts" in Examples and Comparative Examples refer to parts by mass when not specifically stated.

Production Example 1

(Preparation of Ascorbic Acid Aqueous Solution)

Under a nitrogen atmosphere, 30.6 g of L-ascorbic acid, 46.2 g of a 15 mass % aqueous solution of sodium hydroxide, and 4.8 g of ferrous sulfate heptahydrate were mixed to prepare an ascorbic acid aqueous solution of 2.13 mmol/g.

Production Example 2

(Preparation of Dehydroascorbic Acid Aqueous Solution)

Under a nitrogen atmosphere, 4.5 g of dehydroascorbic acid, 6.9 g of a 15 mass % aqueous solution of sodium hydroxide, 0.7 g of ferrous sulfate heptahydrate were mixed to prepare a dehydroascorbic acid aqueous solution of 2.13 mmol/g.

Example 1

Under a nitrogen atmosphere, 10 g of activated carbon, 15 g of polyethylene powder, and 4.7 g of sodium carbonate were weighed and mixed. To the mixed powder, 10.1 g of the ascorbic acid aqueous solution and 10.1 g of the dehydroascorbic acid aqueous solution were added and mixed to produce a deoxygenation agent composition. An aluminum bag was filled with 6.9 g of the deoxygenation agent composition and sealed.

The aluminum bag containing the deoxygenation agent described above was sealed in a nylon bag with 750 mL of air, and the aluminum bag was opened in the nylon bag to initiate a deoxygenation experiment. When the oxygen concentration and the carbon dioxide concentration after 3 hours were measured using a gas chromatograph, the oxygen concentration was 0.20 volume % and the carbon dioxide concentration was 13.6 volume %. In addition, when the oxygen concentration and the carbon dioxide concentration after 24 hours were measured using a gas chromatograph, the oxygen concentration was 0.00 volume % and the carbon dioxide concentration was 13.7 volume %.

Example 2

Under a nitrogen atmosphere, 10 g of activated carbon, 15 g of polyethylene powder, and 4.7 g of sodium carbonate were weighed and mixed. To the mixed powder, 20.3 g of the dehydroascorbic acid aqueous solution was added and mixed to produce a deoxygenation agent composition. An aluminum bag was filled with 6.9 g of the deoxygenation agent composition and sealed.

The aluminum bag containing the deoxygenation agent described above was sealed in a nylon bag with 750 mL of air, and the aluminum bag was opened in the nylon bag to initiate a deoxygenation experiment. When the oxygen concentration and the carbon dioxide concentration after 3 hours were measured using a gas chromatograph, the oxygen concentration was 0.10 volume % and the carbon dioxide concentration was 18.5 volume %. In addition, when the oxygen concentration and the carbon dioxide concentration after 24 hours were measured using a gas chromatograph, the oxygen concentration was 0.00 volume % and the carbon dioxide concentration was 18.6 volume %.

Comparative Example 1

Under a nitrogen atmosphere, 10 g of activated carbon, 15 g of polyethylene powder, and 4.7 g of sodium carbonate were weighed and mixed. To the mixed powder, 20.3 g of the ascorbic acid aqueous solution was added and mixed to produce a deoxygenation agent composition. An aluminum bag was filled with 6.9 g of the deoxygenation agent composition and sealed.

The aluminum bag containing the deoxygenation agent described above was sealed in a nylon bag with 750 mL of air, and the aluminum bag was opened in the nylon bag to initiate a deoxygenation experiment. When the oxygen concentration and the carbon dioxide concentration after 3 hours were measured using a gas chromatograph, the oxygen concentration was 0.55 volume % and the carbon dioxide concentration was 10.7 volume %. In addition, when the oxygen concentration and the carbon dioxide concentration after 24 hours were measured using a gas chromatograph, the oxygen concentration was 0.00 volume % and the carbon dioxide concentration was 11.0 volume %.

The invention claimed is:

1. A gas concentration regulator composition for use in culture of anaerobic bacteria, comprising: (a) dehydroascorbic acid; (b) an ascorbic acid component; (c) a transition metal catalyst; (d) activated carbon; (e) at least one selected from the group consisting of an alkali metal carbonate, an alkali metal hydroxide, and an alkaline earth metal hydroxide; and (f) water,
   wherein a molar ratio [(b)/(a)] of (b) the ascorbic acid component to (a) the dehydroascorbic acid is 1.5 or less.

2. The gas concentration regulator composition for use in culture of anaerobic bacteria according to claim 1, wherein the molar ratio [(b)/(a)] is 1.2 or less.

3. A method for culturing anaerobic bacteria in a sealed container, comprising culturing the anaerobic bacteria in the presence of the gas concentration regulator composition according to claim 1.

4. A gas concentration regulator package, in which the gas concentration regulator composition according to claim 1 is bagged in an individual bag comprising an air-permeable packaging material.

* * * * *